US00PP25057P2

(12) United States Plant Patent
Dummen

(10) Patent No.: US PP25,057 P2
(45) Date of Patent: Nov. 11, 2014

(54) ***OSTEOSPERMUM* PLANT NAMED 'DUETISWELAV'**

(50) Latin Name: *Osteospermum ecklonis*
Varietal Denomination: Duetiswelav

(71) Applicant: Tobias Dummen, Rheinberg (DE)

(72) Inventor: Tobias Dummen, Rheinberg (DE)

(73) Assignee: Dümmen Group B.V., De Lier (NL)

( * ) Notice: Subject to any disclaimer, the term of this patent is extended or adjusted under 35 U.S.C. 154(b) by 64 days.

(21) Appl. No.: 13/815,026

(22) Filed: Jan. 26, 2013

(51) Int. Cl.
*A01H 5/00* (2006.01)

(52) U.S. Cl.
USPC ..... Plt./360

(58) Field of Classification Search
CPC ..... A01H 1/00; A01H 3/00; A01H 4/00; A01H 5/00
USPC ..... Plt./360
See application file for complete search history.

*Primary Examiner* — Anne Grunberg
(74) *Attorney, Agent, or Firm* — C. A. Whealy

(57) ABSTRACT

A new and distinct cultivar of *Osteospermum* plant named 'Duetiswelav', characterized by its compact, upright and mounded plant habit; freely branching growth habit; dense and bushy plant form; early and freely flowering habit; and daisy-type inflorescences with elongated oblong-shaped ray florets that light red purple in color.

1 Drawing Sheet

Botanical designation: *Osteospermum ecklonis.*
Cultivar denomination: 'DUETISWELAV'.

BACKGROUND OF THE INVENTION

The present invention relates to a new and distinct cultivar of *Osteospermum* plant, botanically known as *Osteospermum ecklonis* and hereinafter referred to by the name 'Duetiswelav'.

The new *Osteospermum* plant is a product of a planned breeding program conducted by the Inventor in Rheinberg, Germany. The objective of the program is to create and develop new compact *Osteospermum* plants with uniformly mounded plant habit and numerous attractive inflorescences.

The new *Osteospermum* plant originated from a cross-pollination conducted by the Inventor in July, 2004 of a proprietary selection of *Osteospermum ecklonis* identified as code number Q02-0016-005, not patented, as the female, or seed, parent with a proprietary selection of *Osteospermum ecklonis* identified as code number F-1906-015, not patented, as the male, or pollen, parent. The new *Osteospermum* plant was discovered and selected by the Inventor as a single flowering plant from within the progeny of the stated cross-pollination in a controlled greenhouse environment in Rheinberg, Germany in May, 2006.

Asexual reproduction of the new *Osteospermum* plant by terminal cuttings in a controlled environment in Rheinberg, Germany since June, 2006 has shown that the unique features of this new *Osteospermum* plant are stable and reproduced true to type in successive generations.

SUMMARY OF THE INVENTION

Plants of the new *Osteospermum* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Duetiswelav'. These characteristics in combination distinguish 'Duetiswelav' as a new and distinct *Osteospermum* plant:

1. Compact, upright and mounded plant habit.
2. Freely branching growth habit; dense and bushy plant form.
3. Early and freely flowering habit.
4. Daisy-type inflorescences with elongated oblong-shaped ray florets that are light red purple in color.

In side-by-side comparisons conducted in Rheinberg, Germany, plants of the new *Osteospermum* differ primarily from plants of the female parent selection in ray floret color as ray florets of plants of the female parent selection are white in color.

In side-by-side comparisons conducted in Rheinberg, Germany, plants of the new *Osteospermum* differ primarily from plants of the male parent selection in ray floret color as ray florets of plants of male parent selection are orange in color.

Plants of the new *Osteospermum* can be compared to plants of the *Osteospermum ecklonis* 'Cape Daisy Kalanga Lavender', not patented. In side-by-side comparisons, plants of the new *Osteospermum* differed primarily from plants of 'Cape Daisy Kalanga Lavender' in the following characteristics:

1. Plants of the new *Osteospermum* had longer internodes than plants of 'Cape Daisy Kalanga Lavender'.
2. Inflorescences of plants of the new *Osteospermum* had larger and more ray florets than inflorescences of plants of 'Cape Daisy Kalanga Lavender'.
3. Plants of the new *Osteospermum* had longer peduncles than plants of 'Cape Daisy Kalanga Lavender'.

BRIEF DESCRIPTION OF THE PHOTOGRAPH

The accompanying photograph illustrates the overall appearance of the new *Osteospermum* plant showing the colors as true as it is reasonably possible to obtain in colored reproductions of this type. Colors in the photograph may differ slightly from the color values cited in the detailed botanical description which accurately describe the colors of the new *Osteospermum* plant.

The photograph comprises a side perspective view of a typical flowering plant of 'Duetiswelav' grown in a container.

DETAILED BOTANICAL DESCRIPTION

The aforementioned photograph, following observations and measurements describe plants grown during the spring in 12-cm containers in a glass-covered greenhouse in Rheinberg, Germany and under cultural practices typically used in commercial *Osteospermum* production. During the production of the plants, day and night temperatures averaged 18° C. and light levels averaged 4,500 lux. Measurements and numerical values represent averages for typical flowering plants. Plants were pinched one time about three weeks after planting and were 13 weeks old when the photograph and description were taken. In the following description, color references are made to The Royal Horticultural Society Colour Chart, 1995 Edition, except where general terms of ordinary dictionary significance are used.

Botanical classification: *Osteospermum ecklonis* 'Duetiswelav'.

Parentage:

*Female, or seed, parent*.—Proprietary selection of *Osteospermum ecklonis* identified as code number Q02-0016-005, not patented.

*Male, or pollen, parent*.—Proprietary selection of *Osteospermum ecklonis*, identified as code number F-1906-015, not patented.

Propagation:

*Type*.—Terminal vegetative cuttings.

*Time to initiate roots, summer*.—About five days at temperatures about 20° C.

*Time to initiate roots, winter*.—About seven days at temperatures about 20° C.

*Time to produce a rooted young plant, summer*.—About three weeks at temperatures about 20° C.

*Time to produce a rooted young plant, winter*.—About four weeks at temperatures about 20° C.

*Root description*.—Fine, fibrous; white in color.

*Rooting habit*.—Freely branching; dense.

Plant description:

*Plant and growth habit*.—Compact, upright and mounded plant habit; upright inflorescences positioned above the foliar plane; freely branching habit with about four lateral branches developing per plant; pinching enhances lateral branch development; dense and bushy plant form; and moderately vigorous growth habit.

*Plant height*.—About 15 cm.

*Plant diameter*.—About 14 cm.

*Lateral branches*.—Length: About 27 cm. Diameter: About 6 mm. Internode length: About 1.1 cm. Strength: Strong. Texture: Smooth, glabrous. Color: Close to 144B.

*Foliage description*.—Arrangement: Alternate, simple. Length: About 5.5 cm. Width: About 1.8 cm. Shape: Roughly spatulate. Apex: Acute. Base: Attenuate. Margin: Dentate. Texture, upper and lower surfaces: Pubescent; leathery. Venation pattern: Pinnate. Color: Developing leaves, upper surface: Close to 137B. Developing leaves, lower surface: Close to 144A. Fully expanded leaves, upper surface: Close to 137A; venation, close to 144B. Fully expanded leaves, lower surface: Close to 137B; venation, close to 144B. Petioles: Length: About 6.6 mm. Diameter: About 5.8 mm. Texture, upper and lower surfaces: Smooth, glabrous. Color, upper surface: Close to 144C. Color, lower surface: Close to 144A.

Inflorescence description:

*Appearance and flowering habit*.—Daisy-type inflorescence form with elongated oblong-shaped ray florets; inflorescences mostly flat and are positioned above the foliar plane on strong peduncles; disc and ray florets developing acropetally on a capitulum; inflorescences face mostly upright; freely flowering habit with about 50 inflorescences developing per plant.

*Fragrance*.—None detected.

*Natural flowering season and flowering response*.—In Germany, plants of the new *Osteospermum* flower continuously during the spring and summer; early flowering habit, plants begin flowering about six weeks after planting.

*Flower longevity*.—Inflorescences last about three days on the plant; inflorescences not persistent.

*Inflorescence buds*.—Height: About 4.6 mm. Diameter: About 7.3 mm. Shape: Ovoid. Color: Close to 137B and 154B.

*Inflorescence size*.—Diameter: About 6 cm. Depth (height): About 2.25 cm. Disc diameter: About 10.5 mm. Receptacle diameter: About 4.4 mm. Receptacle height: About 3.4 mm.

*Ray florets*.—Quantity and arrangement: About 28 per inflorescence arranged in one to two whorls. Length: About 3.1 cm. Width: About 8.4 mm. Shape: Elongated oblong. Apex: Emarginate. Base: Obtuse. Margin: Entire. Texture, upper and lower surfaces: Smooth, glabrous. Color: When opening and fully opened, upper surface: Close to 74D; color becoming closer to 75C with development. When opening and fully opened, lower surface: Longitudinal stripes, close to 88D and 84D.

*Disc florets*.—Quantity and arrangement: About 32 per inflorescence massed at the center of the receptacle. Length: About 6 mm. Diameter, apex: About 1 mm. Diameter, base: About 0.8 mm. Shape: Tubular; apex dentate, five-pointed. Color: Towards the apex, close to 90A; towards the base, close to 1D.

*Phyllaries*.—Quantity per inflorescence: About 17 to 20. Length: About 8 mm. Width: About 2 mm. Shape: Lanceolate. Apex: Apiculate. Base: Acute. Margin: Entire. Texture, upper and lower surfaces: Smooth, glabrous; leathery. Color, upper surface: Close to 137B. Color, lower surface: Close to 137C.

*Peduncles*.—Length: About 6.5 cm. Diameter: About 2 mm. Strength: Strong. Aspect: Mostly upright. Texture: Smooth, glabrous; leathery. Color: Close to 144A.

*Reproductive organs*.—Androecium: Present on disc florets only. Anther shape: Oval. Anther length: About 2 mm. Anther color: Close to 97A. Pollen amount: Abundant. Pollen color: Close to 17A. Gynoecium: Present on both ray and disc florets. Pistil length: About 4 mm. Stigma shape: Crested. Stigma color: Close to 79A. Style length: About 3 mm. Style color: Close to 79A. Ovary color: Close to 144C.

*Seeds*.—Length: About 6.4 mm. Diameter: About 2.8 mm. Color: Close to 200A.

Disease & pest resistance: Plants of the new *Osteospermum* have not been shown to be resistant to pathogens and pests common to *Osteospermum* plants.

Temperature tolerance: Plants of the new *Osteospermum* have been observed to tolerate temperatures ranging from about 5° C. to about 35° C.

It is claimed:

1. A new and distinct *Osteospermum* plant named 'Duetiswelav' as illustrated and described.

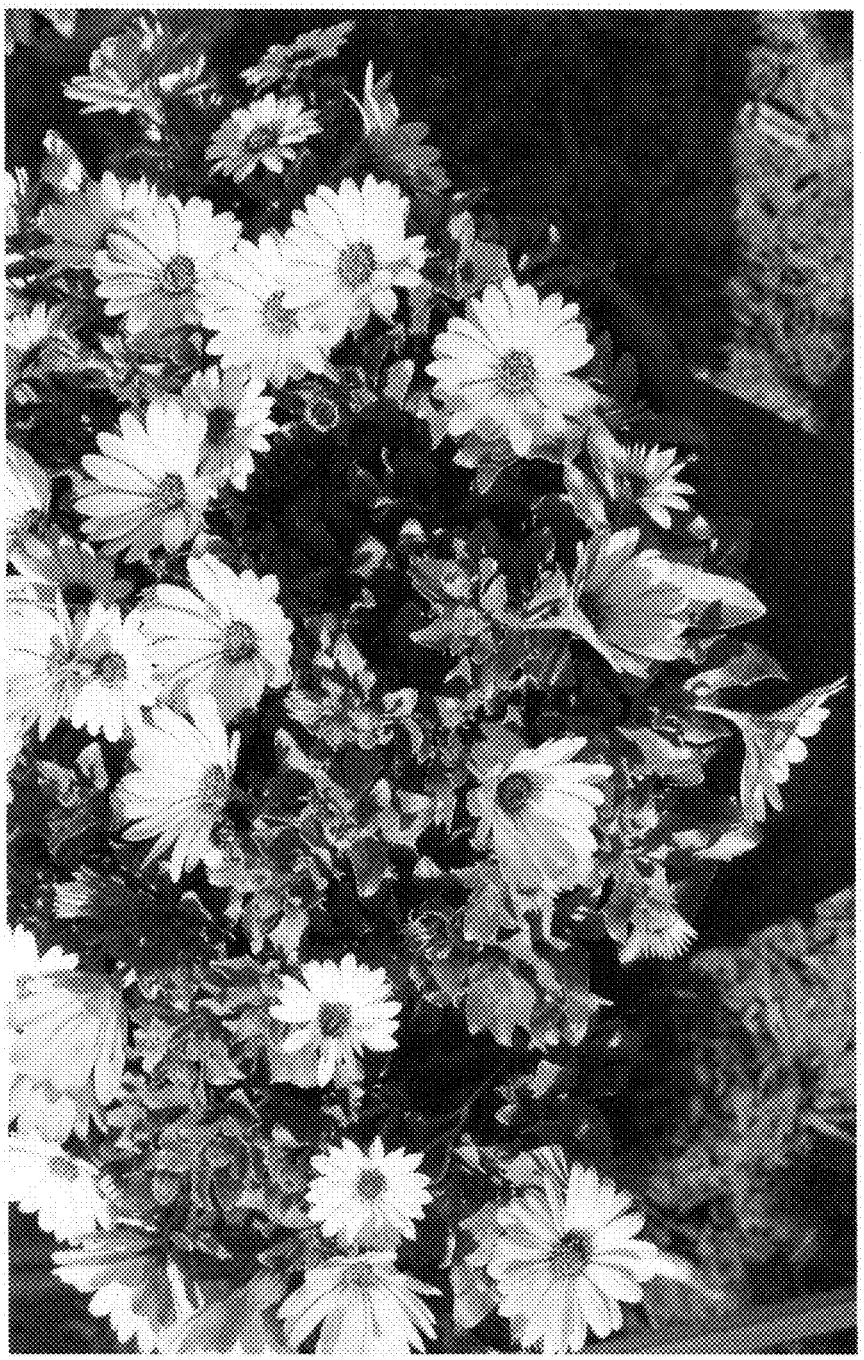

* * * * *